US 8,764,772 B2

(12) United States Patent
Tekulve

(10) Patent No.: US 8,764,772 B2
(45) Date of Patent: Jul. 1, 2014

(54) OCCLUSION DEVICE

(75) Inventor: Kurt J. Tekulve, Ellettsville, IN (US)

(73) Assignee: Cook Medical Technologies LLC, Blommington, IN (US)

( * ) Notice: Subject to any disclaimer, the term of this patent is extended or adjusted under 35 U.S.C. 154(b) by 1367 days.

(21) Appl. No.: 12/034,719

(22) Filed: Feb. 21, 2008

(65) Prior Publication Data
US 2009/0216263 A1 Aug. 27, 2009

(51) Int. Cl.
*A61B 17/08* (2006.01)

(52) U.S. Cl.
USPC .......................................... 606/151; 606/157

(58) Field of Classification Search
CPC ................... A61B 17/12172; A61B 17/12177; A61F 2230/001
USPC .................. 606/157, 151, 200, 213; 623/1.15
See application file for complete search history.

(56) References Cited

U.S. PATENT DOCUMENTS

| | | | |
|---|---|---|---|
| 4,580,568 A | 4/1986 | Gianturco | |
| 5,035,706 A | 7/1991 | Giantureo et al. | |
| 5,499,995 A | 3/1996 | Teirstein | |
| 5,507,767 A | 4/1996 | Maeda et al. | |
| 5,683,411 A * | 11/1997 | Kavteladze et al. | 606/200 |
| 5,766,160 A * | 6/1998 | Samson et al. | |
| 5,846,261 A * | 12/1998 | Kotula et al. | 606/213 |
| 5,861,003 A * | 1/1999 | Latson et al. | 606/213 |
| 5,919,224 A * | 7/1999 | Thompson et al. | 606/200 |
| 6,042,606 A | 3/2000 | Frantzen | |
| 6,368,338 B1 * | 4/2002 | Konya et al. | 606/200 |
| 6,428,550 B1 | 8/2002 | Vargas et al. | |
| 6,468,303 B1 | 10/2002 | Amplatz et al. | |
| 6,582,447 B1 | 6/2003 | Patel et al. | |
| 6,599,308 B2 | 7/2003 | Amplatz | |
| 6,638,257 B2 | 10/2003 | Amplatz | |
| 6,682,546 B2 | 1/2004 | Amplatz | |
| 6,790,220 B2 * | 9/2004 | Morris et al. | 606/213 |
| 7,001,409 B2 | 2/2006 | Amplatz | |
| 7,195,636 B2 | 3/2007 | Avellanet et al. | |
| 2002/0123759 A1 | 9/2002 | Amplatz | |
| 2002/0198561 A1 | 12/2002 | Amplatz | |
| 2005/0004598 A1 | 1/2005 | White, Jr. et al. | |
| 2005/0055082 A1 | 3/2005 | Ben Muvhar et al. | |
| 2006/0247680 A1 | 11/2006 | Amplatz et al. | |
| 2007/0265656 A1 | 11/2007 | Amplatz et al. | |

OTHER PUBLICATIONS

U.S. Appl. No. 60/903,791, filed Feb. 27, 2007, Hoffman.
U.S. Appl. No. 11/762,570, filed Jun. 13, 2007, Hardert, et al.
U.S. Appl. No. 11/845,446, filed Aug. 27, 2007, Tekulve.
U.S. Appl. No. 11/845,452, filed Aug. 27, 2007, Brumleve et al.
U.S. Appl. No. 11/845,455, Aug. 27, 2007, Hardert et al.
U.S. Appl. No. 11/848,782, filed Aug. 31, 2007, Kurrus.

* cited by examiner

*Primary Examiner* — Gregory Anderson
(74) *Attorney, Agent, or Firm* — Brinks Gilson & Lione

(57) ABSTRACT

An occlusion device for occluding a body vessel is provided. The occlusion device has a tubular expandable body having an interior side and an exterior side. A restricting ring is located around the exterior side of the tubular expandable body and collapses a portion of the tubular expandable body. The occlusion device is configured to move between an expanded state for occlusion within a body vessel and a collapsed state for delivery or retrieval of the device, and the device is configured to open radially to define the expanded state and to collapse along the longitudinal axis to define the collapsed state. A delivery assembly for an occlusion device and a method of constructing an occlusion device are also disclosed.

25 Claims, 10 Drawing Sheets

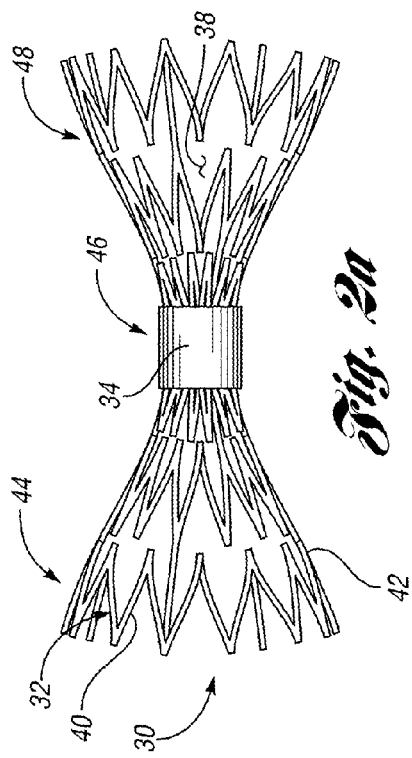
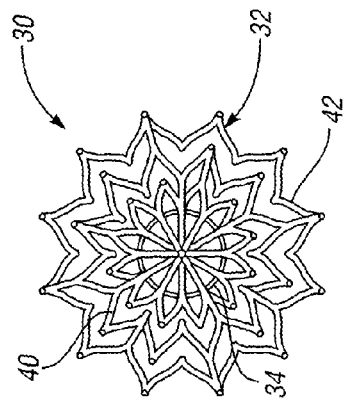
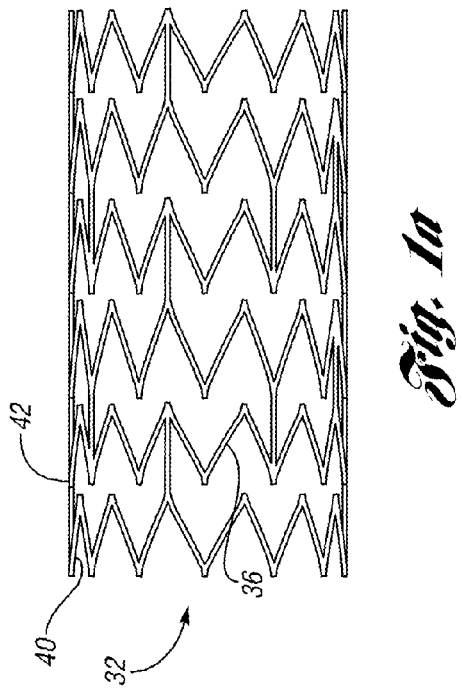
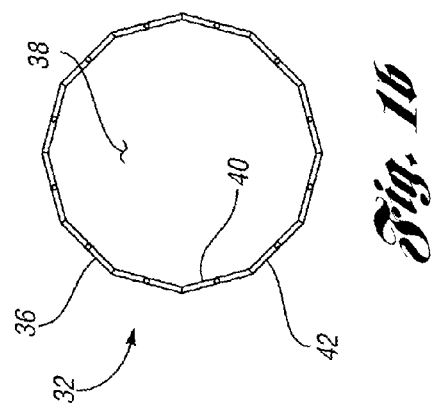

OCCLUSION DEVICE

BACKGROUND

1. Field of the Invention

The present invention generally relates to vascular occlusion devices. More specifically, the invention relates to occlusion devices having an expandable body.

2. Description of Related Art

A number of different devices may be used to occlude a body cavity, for example, a blood vessel. When it is desirable to quickly occlude a blood vessel, an inflatable balloon may be used. However, balloons have the disadvantage of being temporary. Another example of an occlusion device includes embolization coils. Embolization coils may be permanent and promote blood clots or tissue growth over a period of time, thereby occluding the body cavity. In conjunction with the embolization coil, a spider shaped vascular obstruction device may be used to prevent dislodgment of the embolization coils while the blood clots or the tissue grows. A problem with this arrangement is that blood may continue to flow past the coil and spider shaped device and through the body cavity until it finally occludes. It may take a significant period of time for sufficient clotting or tissue growth to fully occlude the body cavity. This leaves a patient open to a risk of injury from the condition which requires the body cavity to be occluded. Also, this arrangement is more complex since it requires the delivery of two or more separate devices to the vasculature.

In view of the above, it is apparent that there exists a need for an improved vascular occlusion device capable of occluding a body vessel quickly.

SUMMARY

In satisfying the above need, as well as overcoming the enumerated drawbacks and other limitations of the related art, the present invention provides an improved occlusion device for occluding a body vessel.

In one form, the occlusion device includes a tubular expandable body having an interior side and an exterior side. A restricting ring is located around the exterior side of the tubular expandable body and collapses a portion of the tubular expandable body. The occlusion device is configured to move between an expanded state for occlusion within a body vessel and a collapsed state for delivery or retrieval of the device, and the device is configured to open radially to define the expanded state and to collapse along the longitudinal axis to define the collapsed state.

In another form, the occlusion device includes a tubular expandable body defining a lumen through a center of the tubular expandable body and a restricting ring disposed around the tubular expandable body. The restricting ring collapses a portion of the tubular expandable body to substantially close the lumen of the tubular expandable body. The occlusion device is configured to move between an expanded state for occlusion within a body vessel and a collapsed state for delivery or retrieval of the device, and the device is configured to open radially to define the expanded state and to collapse along the longitudinal axis to define the collapsed state.

The present invention also encompasses a delivery assembly for placing and retrieving one of the occlusion devices described herein into a body vessel. The assembly includes an outer sheath having a tubular body extending from a proximal part to a distal part and including a sheath lumen. An inner member extends from a proximal portion to a distal portion and is disposed within the sheath lumen and configured for axial movement relative to the outer sheath. The occlusion device is coaxially disposed within the sheath lumen and removably coupled to the distal portion of the inner member and is deployable through the distal part of the outer sheath by means of the relative axial movement of the inner member. The occlusion device includes any of the devices described herein. In one embodiment of the assembly, the distal portion of the inner member includes a threaded section.

The present invention also includes a method of constructing an occlusion device for occluding a body vessel. The method includes cutting a tubular expandable body from a frame to form the tubular expandable body defining a lumen along a longitudinal axis through a center of the tubular expandable body. The method further includes attaching a restricting ring around an exterior side of the tubular expandable body.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 1a is a side view of a tubular expandable body that may be used to form an occlusion device in accordance with the principles of the present invention;

FIG. 1b is an end view of the tubular expandable body of FIG. 1a, in accordance with the principles of the present invention;

FIG. 2a is a side view of an occlusion device embodying the principles of the present invention, which includes the tubular expandable body of FIGS. 1a-1b;

FIG. 2b is an end view of the occlusion device of FIG. 2a, in accordance with the principles of the present invention;

DETAILED DESCRIPTION

Figure 3:
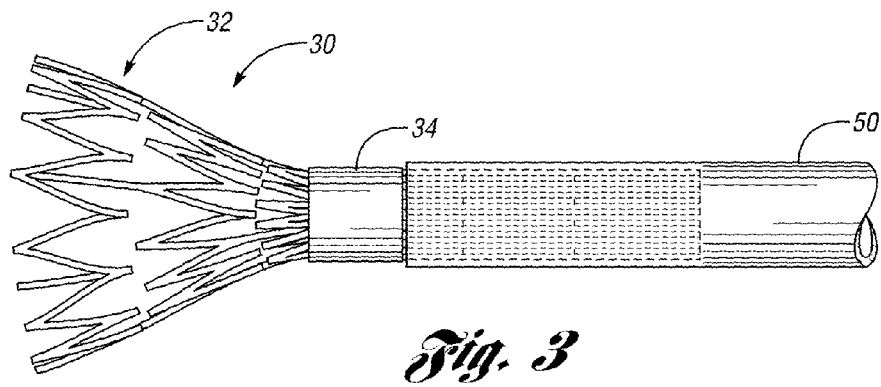
FIG. 3 is a side view of the occlusion device of FIGS. 2a and 2b partially collapsed inside of a catheter sheath in accordance with the principles of the present invention.

The terms "about" or "substantially" used herein with reference to a quantity includes variations in the recited quantity that are equivalent to the quantity recited, such as an amount that is insubstantially different from a recited quantity for an intended purpose or function.

Referring now to FIGS. 2a and 2b, a first embodiment of an occlusion device for occluding a body vessel or another body lumen, such as an aneurysm, is illustrated therein and designated at 30. As its primary components, the occlusion device 30 includes a tubular expandable body 32 having a restricting ring 34 disposed around it.

The tubular expandable body 32 of the occlusion device 30 may resemble a stent, as shown in FIGS. 1a and 1b, wherein the tubular expandable body 32 comprises a frame having a plurality of members 36, such as wires, that are interconnected and configured to expand into an open configuration and are collapsible into a collapsed configuration. The members 36 of the frame define a lumen 38 therethrough. As such, the tubular expandable body 32 has an interior side 40 and an exterior side 42. Preferably, the tubular expandable body 32 is cylindrical, although other configurations may be used, without falling beyond the spirit and scope of the present invention. Although the members 36 of the tubular expandable body 32 are shown having zigzag shapes, many other configurations may be suitable, such as those disclosed in U.S. Pat. No. 4,580,568; U.S. Pat. No. 5,035,706; U.S. Pat. No. 5,507,767; and U.S. Pat. No. 6,042,606 all of which are incorporated herein by reference in their entireties. For example, the members 36 could alternatively have a sinusoidal shape or a criss-cross pattern. The tubular expandable body 32 could be formed in different ways, which also affects its configuration. For example, the tubular expandable body could be cut from a thin solid tube, such that it expands to a much larger tube having a lumen formed therethrough. In such a configuration, the tubular expandable body 32 is collapsible down to nearly the size of the original thin solid tube that it was formed from. In the alternative, the tubular expandable body could be formed from a plurality of braided members.

The tubular expandable body 32 may be made of any suitable material, for example, a superelastic material, a nickel-based superalloy, stainless steel wire, cobalt-chromium-nickel-molybdenum-iron alloy, cobalt chrome-alloy, stress relieved metal (e.g., platinum), or nickel-based superalloys, such as Inconel. The tubular expandable body 32 may preferably be formed of any appropriate material that will result in a self-expanding device 30 capable of being percutaneously inserted and deployed within a body cavity, such as shape memory material. Shape memory materials or alloys have the desirable property of becoming rigid, i.e., returning to a remembered state, when heated above a transition temperature. A shape memory alloy suitable for the present invention is nickel-titanium (Ni—Ti) available under the more commonly known name Nitinol. When this material is heated above the transition temperature, the material undergoes a phase transformation from martensite to austenite, such that the material returns to its remembered state. The transition temperature is dependent on the relative proportions of the alloying elements Ni and Ti and the optional inclusion of alloying additives. The Nitinol could be of various types, such as linear elastic Nitinol or radiopaque Nitinol.

In one embodiment, the tubular expandable body 32 is made from Nitinol with a transition temperature that is slightly below normal body temperature of humans, which is about 98.6° F. Thus, when the device 30 is deployed in a body vessel and exposed to normal body temperature, the alloy of the tubular expandable body 32 will transform to austenite, that is, the remembered state, which for one embodiment of the present invention is the expanded state when the device 30 is deployed in the body vessel. To remove the device 30, it is cooled to transform the material to martensite which is more ductile than austenite, making the tubular expandable body 32 more malleable. As such, the device 30 can be more easily collapsed and pulled into a lumen of a catheter for removal.

In another embodiment, the tubular expandable body 32 is made from Nitinol with a transition temperature that is above normal body temperature of humans, which is about 98.6° F. Thus, when the device 30 is deployed in a body vessel and exposed to normal body temperature, the tubular expandable body 32 is in the martensitic state so that the tubular expandable body 32 is sufficiently ductile to bend or form into a desired shape, which for the present embodiment is the expanded state. To remove the device 30, the device 30 is heated to transform the alloy of the tubular expandable body 32 to austenite so that it becomes rigid and returns to a remembered state, which for the device 30 is a collapsed state.

With reference to FIG. 2a, the tubular expandable body 32 may be described as having a distal portion 44, a middle portion 46, and a proximal portion 48, with the middle portion 46 being located between the proximal and distal portions 48, 44. The proximal and distal portions 48, 44 each have open ends, in this embodiment. The restricting ring 34 is located around the exterior side 42 of the tubular expandable body 32 and collapses a portion of the tubular expandable body 32. In FIGS. 2a and 2b, the middle portion 46 of the tubular expandable body 32 is collapsed by the restricting ring 34. This results in the middle portion 46 having a diameter that is smaller than the diameters of the proximal and distal portions 44, 48, in the expanded state. In other words, the middle portion 46 has a diameter smaller than the diameters of each of the open ends. In this embodiment, the open ends, or the proximal and distal portions 48, 44, have diameters that are about equal.

The restricting ring 34 is wrapped around the exterior side 42 of the middle portion 46 of the tubular expandable body 32 to substantially close the lumen 38 of the tubular expandable body 32. The lumen 38 is not necessarily completely closed (although it could be), but in this embodiment the lumen 38 may be collapsed to close a majority of the through-channel of the lumen 38, so that occlusion of the body vessel may occur. The occlusion device 30 may be described as having an hour glass shape, or a bow tie shape, in this embodiment, such that the proximal and distal portions 44, 48 are larger than the middle portion 46.

The restricting ring 34 is preferably one of a marker band, a stitch, an SIS strand (described in further detail below), a fabric ring, a thread, a wire, a flexible tube, a portion of a cannula, or an elastic band. In FIGS. 2a-4, the restricting ring 34 is shown as a marker band, which is preferably a radiopaque marker band to assist with identification of a percutaneously deployed device 30. However, the restricting ring 34 may be of any suitable material to collapse a portion of the tubular expandable body 32 so that a portion of the expandable tubular body 32 is drawn toward the center of its lumen 38 and away from a vessel wall when deployed in a body vessel. Other variations of the restricting ring 34 could also have radiopaque qualities to assist with identification, or they could have eyelets or other attachment mechanisms for radiopaque materials. Furthermore, identification eyelets could be located on the tubular expandable body 32.

In some embodiments, the restricting ring 32 may be hooked into the structure of the tubular expandable body 32, which may help secure the restricting ring 34 to the tubular expandable body 32. In addition, or in the alternative, the restricting ring 34 could be attached by crimping, by placing it in a dimpled section of the tubular expandable body 32, by tying it around the tubular expandable body 32, by securing it with adhesive, by attaching it with barbs or hooks, by stitching it onto the tubular expandable body 32, or by attaching it in any other suitable manner.

Figure 4:
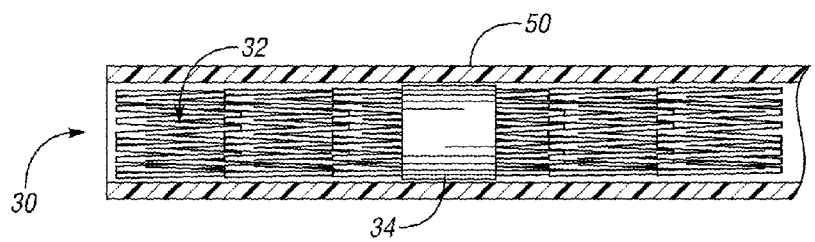
FIG. 4 is a cross-sectional view of the catheter sheath of FIG. 3, showing the occlusion device of FIGS. 2a, 2b, and 3, the occlusion device being collapsed inside of the catheter sheath in accordance with the principles of the present invention.

With reference to FIGS. 2a, 2b, 3 and 4, the occlusion device 30 is configured to move between an expanded state for occlusion within a body vessel and a collapsed state for delivery or retrieval of the device 30. The device 30 is configured to open radially to define the expanded state and to collapse along a central longitudinal axis, which extends through the lumen 38, to define the collapsed state. In FIGS. 2a-2b, the occlusion device 30 is shown in the expanded state. In FIG. 3, the device 30 is partially located within a sheath 50, wherein a portion of the device 30 is collapsed and a portion of the device 30 is expanded. In FIG. 4, the device 30 is collapsed within the sheath 50 in the collapsed state. Even in the expanded state of the device 30, the middle portion 46 of the tubular expandable body 32 is collapsed by the restricting ring 34.

Figure 5:
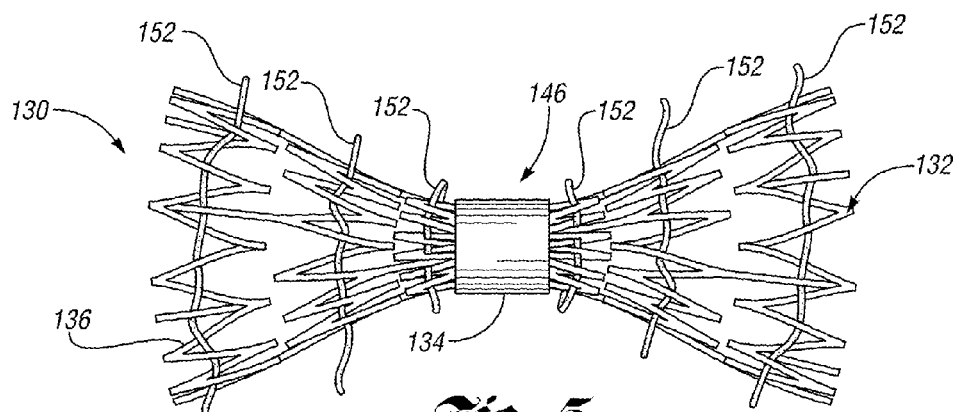
FIG. 5 is a side view of another occlusion device according to the principles of the present invention.

With reference to FIG. 5, another occlusion device 130 embodying the principles of the present invention is illustrated. Similarly to the occlusion device 30 of FIGS. 2a-4, the occlusion device 130 of FIG. 5 has a tubular expandable body 132 defining a lumen therethrough, which has middle portion 146 collapsed by a restricting ring 134. In the alternative, portions other than the middle portion 146 may be collapsed by the restricting ring 134, and some of these variations will be described in further detail below. Additionally or alternatively, the device 130 may include any of the variations hereinbefore or hereinafter described.

To enhance embolization, the occlusion device 130 also has a plurality of occluding materials interwoven between members 136 of the tubular expandable body 132. The occluding materials are shown as threads 152; however, any other suitable occluding material may be used. The threads or occluding material may be comprised of one or more of the following: an extracelluar matrix (ECM), such as small intestinal submucosa (SIS), synthetic polyester, such as DACRON™, nylon, rayon, polyester, polytetrafluoroethylene, polyurethane, and bioremodelable material, which could be laminated, if desired. The occluding material may itself be laminated, or it could be laminated to the tubular expandable body 132.

As known, ECM is a complex structural entity surrounding and supporting cells found within tissues. More specifically, ECM includes structural proteins (for example, collagen and elastin), specialized protein (for example, fibrillin, fibronectin, and laminin), and proteoglycans, a protein core to which are attached long chains of repeating disaccharide units termed glycosaminoglycans.

In one particular embodiment, the extracellular matrix is comprised of small intestinal submucosa (SIS). As known, SIS is a resorbable, acellular, naturally occurring tissue matrix composed of extracellular matrix (ECM) proteins and various growth factors. SIS is derived from the porcine jejunum and functions as a remodeling bioscaffold for tissue repair. SIS has characteristics of an ideal tissue engineered biomaterial and can act as a bioscaffold for remodeling of many body tissues including skin, body wall, musculoskeletal structure, urinary bladder, and also supports new blood vessel growth. SIS may be used to induce site-specific remodeling of both organs and tissues depending on the site of implantation. In practice, host cells are stimulated to proliferate and differentiate into site-specific connective tissue structures, which have been shown to completely replace the SIS material in time.

In this embodiment, SIS is attached to the occlusion device 130 to assist with occluding a body vessel, adhere to the walls of the body vessel in which the device 130 is deployed, and promote body tissue growth within the body vessel. SIS has a natural adherence or wetability to body fluids and connective cells comprising the connective tissue of the walls of a body vessel. If the device 130 is intended to permanently occlude the body vessel, the device 130 is positioned such that the host cells of the wall will adhere to the SIS and subsequently differentiate, growing into the SIS and eventually occluding the body vessel with the tissue of the walls to which the device 130 was originally adhered. This feature enhances permanent occlusion of the body vessel. In another particular embodiment, the SIS may be used to temporarily adhere the device 130 to the walls of the body vessel. If the device 130 is only deployed within the body vessel temporarily, host cells of the walls may adhere to the device 130, but will not differentiate, allowing for later retrieval of the device 130 from the body vessel.

The occluding material may be attached to the occlusion device in any suitable manner. For example, with reference to FIG. 6, another occlusion device 230 is illustrated. In this embodiment, the occluding material comprises laminated strips 252 of SIS or Dacron, which extends at an angle through the center of the occlusion device 230, crossing the longitudinal axis of the device 230.

Figure 6:
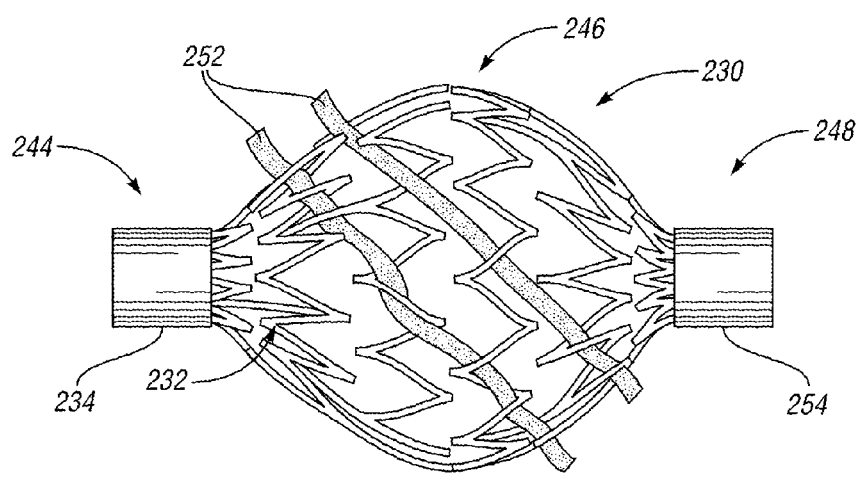
FIG. 6 is a side view of another occlusion device according to the principles of the present invention.

Like the occlusion devices 30, 130 hereinbefore described, the occlusion device 230 of FIG. 6 has a tubular expandable body 232 partially collapsed by a restricting ring 234. However, in this embodiment, one restricting ring 234 is located at the proximal end 244 of the tubular expandable body 232, and a second restricting ring 254 is located at the distal end 248 of the tubular expandable body 232. Thus, the middle portion 246 has a larger diameter than the proximal and distal ends 244, 248.

Figure 7:
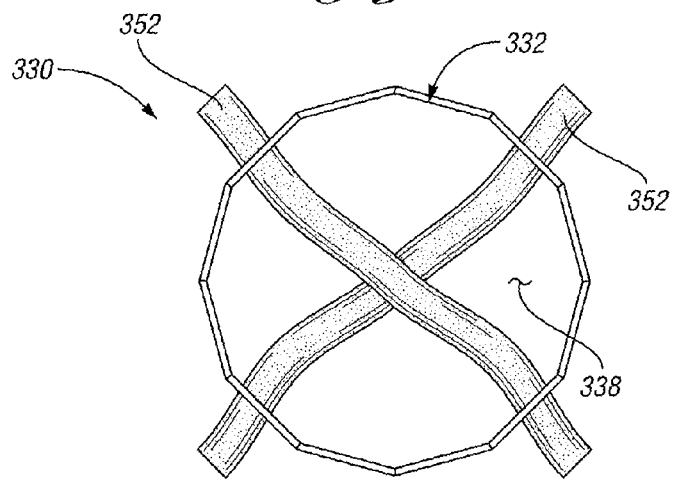
FIG. 7 is a schematic cross-sectional view of yet another occlusion device according to the principles of the present invention.

With reference to FIG. 7, another occlusion device 330 is illustrated, which has occluding material 352 forming a criss-cross pattern through the center of the lumen 338 of the tubular expandable body 332. The occluding material 352 could of any type hereinbefore described. The occlusion device 330 could have any configuration hereinbefore or hereinafter described, including a tubular expandable body 332 and at least one restricting ring (not shown).

Figure 8:
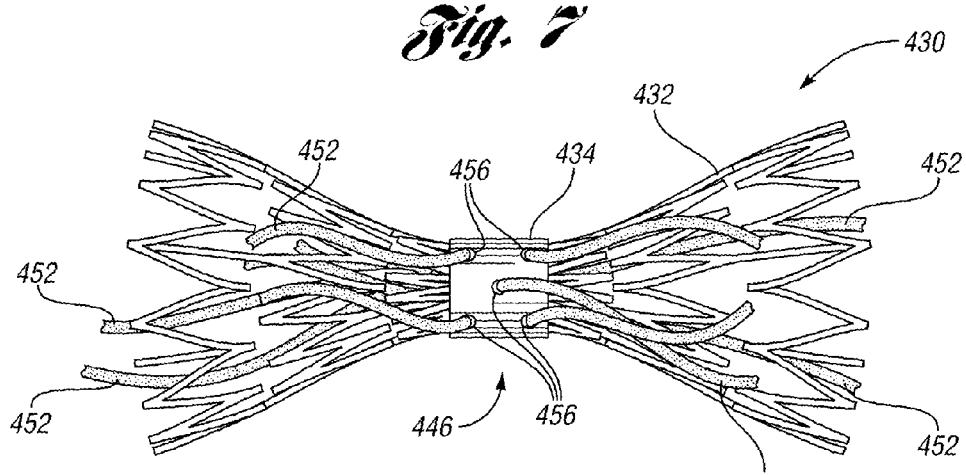
FIG. 8 is a side view of still another occlusion device according to the principles of the present invention.

With reference to FIG. 8, yet another occlusion device 430 embodying the principles of the present invention is illustrated. Like the occlusion devices 30, 130, 230, 330 previously described, the occlusion device 430 has a tubular expandable body 432 having a portion collapsed by a restricting ring 434. The restricting ring 434 collapses a middle portion 446 of the tubular expandable body 332 to form the occlusion device 430. In this embodiment, the restricting ring 434 has a plurality of holes 456 formed therein. Threads 452 of occluding material are threaded through each of the holes 456 to attach the threads 452 to the occlusion device 430. In the alternative, the threads 452 could be threaded under or around the restricting ring 434. In all other respects, the occlusion device 430 may be similar to those hereinbefore or hereinafter described.

Figure 9:
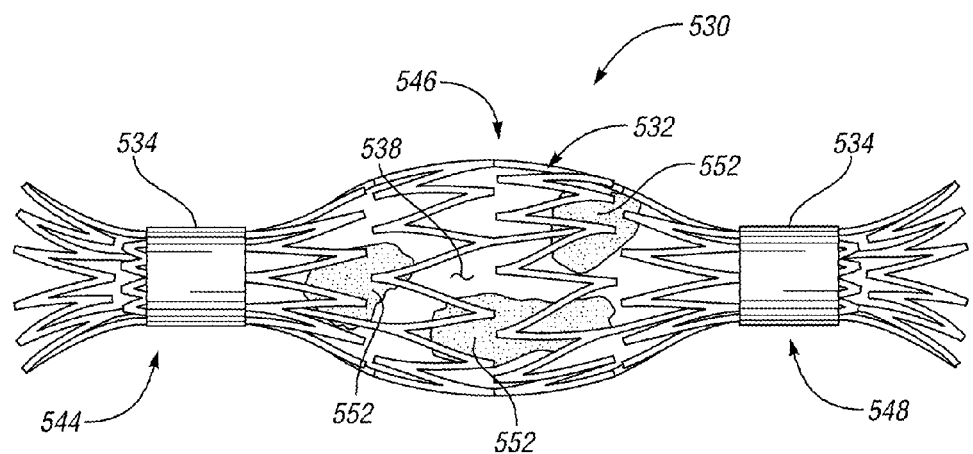
FIG. 9 is a side view of still another occlusion device according to the principles of the present invention.

With reference to FIG. 9, another occlusion device 530 having occluding material 552 is illustrated. The occlusion device 530 has a tubular expandable body 532 having portions partially collapsed by a pair of restricting rings 534. One restricting ring 534 collapses a proximal portion 544 of the tubular expandable body 532 and the other restricting ring 534 collapses a distal portion 548 of the tubular expandable body 532, forming a candy-shaped occlusion device 530. The occluding material 552 takes the form of particles of occluding material located in the middle portion 546 of the occlusion device 530, within the lumen 538 of the tubular expandable body 532 and trapped between the restricting rings 534. The occluding material 552 could be any of the kinds hereinbefore described. In all other respects, the occlusion device 530 may be similar to those hereinbefore or hereinafter described.

Figure 10:
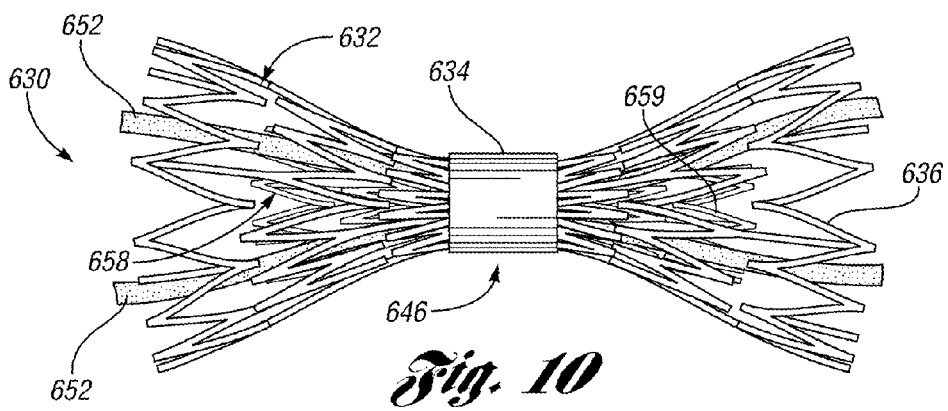
FIG. 10 is a side view of still another occlusion device according to the principles of the present invention.

With reference to FIG. 10, yet another occlusion device 630 according to the principles of the present invention is illustrated. The occlusion device 630 includes an outer tubular expandable body 632 surrounding an inner tubular expandable body 658. Both tubular expandable bodies 632, 658 define lumens therethrough. A restricting ring 634 collapses middle portions 646 of each of the tubular expandable bodies 632, 658 to substantially close the lumens of the tubular expandable bodies 632, 658. Laminated strips 652 of occluding material extend through the lumen of the outer tubular expandable body 632 between the outer tubular expandable body 632 and the inner tubular expandable body 658. The strips 652 of occluding material may be held in place by the restricting ring 634, or they may be held by one or both of the tubular expandable bodies 632, 658.

In embodiments having only one tubular expandable body 632 and no inner tubular expandable body 658, the occluding material strips 652 could still extend through the center of the lumen of the tubular expandable body 632, along a longitudinal axis of the occlusion device 630. For example, the occluding material strips 652 could extend through the center of the tubular expandable body 632 at least partially along the longitudinal axis, with the restricting ring 634 collapsing the middle portion 646 of the tubular expandable body 632 to substantially close the lumen of the tubular expandable body 632 around the occluding material strips 652.

In another embodiment, the occluding material strips 652 could be omitted from the occlusion device 630. Thus, the occlusion device 630 could be comprised of merely the outer tubular expandable body 632, the inner tubular expandable body 658, and the restricting ring 634.

In any of the above-described examples of occlusion devices 630 having an outer tubular expandable body 632 and an inner tubular expandable body 658, it should be understood that each tubular expandable body 632, 658 could be constructed differently, for example, having differently shaped members 636, 659.

Although FIGS. 5-10 show various ways of incorporating occluding material into the occlusion devices of the present invention, still other methods of doing so could be used. For example, occluding material could be tied on or knotted onto any part of the occlusion device 30, 130, 230, 330, 430, 530, 630, it could be mechanically fixated onto the members 36, 136, 636 of the tubular expandable body 32, 132, 232, 332, 432, 532, 632 or the restricting ring 34, 134, 234, 434, 534, 634, adhesive could be used to apply occluding material, the occluding material could be lyophilized to the device 30, 130, 230, 330, 430, 530, 630, or the occluding material could be woven or webbed through the device 30, 130, 230, 330, 430, 530, 630 in various fashions, and it is contemplated that there are other suitable ways of applying occluding material to the occlusion device 30, 130, 230, 330, 430, 530, 630.

Furthermore, in addition to the occluding material hereinbefore described, an occlusion device 30, 130, 230, 330, 430, 530, 630 of the present invention could also or alternatively include a thrombogenic material sprayed on the occlusion device 30, 130, 230, 330, 430, 530, 630 to promote clotting. In another variation, the tubular expandable body 32, 132, 232, 332, 432, 532, 632 could have members 36, 136, 636 having varying amounts of smoothness, wherein rough portions could help promote clotting.

Figure 11:
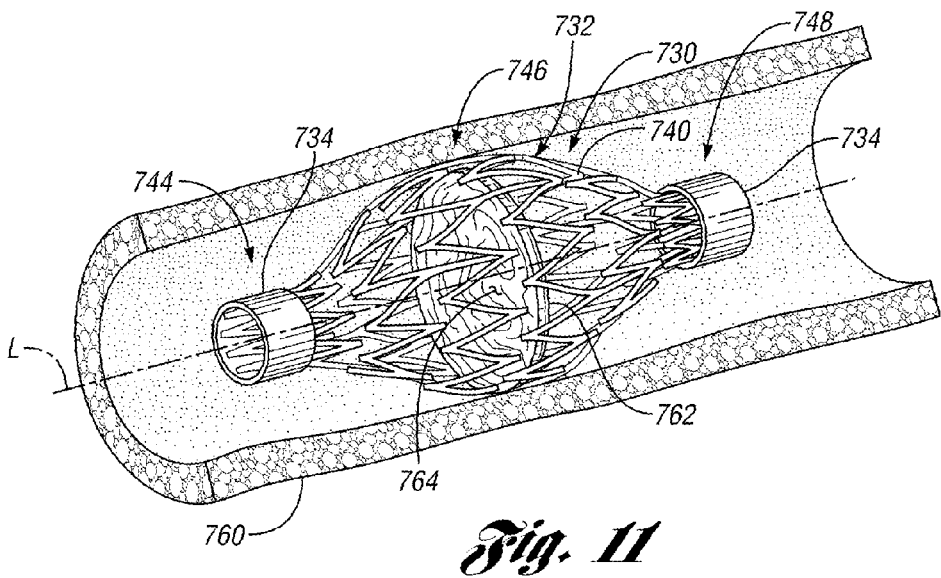
FIG. 11 is a side view of still another occlusion device according to the principles of the present invention, the occlusion device being disposed inside a body vessel.

With reference to FIG. 11, yet another occlusion device 730 is illustrated, in accordance with the principles of the present invention. Similarly to the occlusion device 230 of FIG. 6, the occlusion device 730 of FIG. 10 has a tubular expandable body 732 collapsed at a proximal end 744 and a distal end 748.

In FIG. 11, occluding material is configured as a disk 762 attached to the interior side 740 of the tubular expandable body 732. The disk 762 may contain various materials to aid in occlusion of the body vessel 760. In one embodiment, the occluding material is biocompatible material 764 extending radially around the longitudinal axis to form the disk 762, thereby forming an occluding barrier. The disk 762 may have a thickness substantially smaller than a diameter of the disk 762, the precise proportions of which may vary depending on the needs of a particular application. In various examples, the biocompatible material 764 may be wholly contained within the volume of the disk 762. In other examples, the biocompatible material 764 may only be substantially contained within the volume of the disk 762. In other words, the biocompatible material 764 may extend outward form the disk 762.

In one example, the disk 762 is oriented substantially perpendicular to the longitudinal axis, which is perpendicular to the direction of fluid flow through the vessel 760. In another example, the disk 762 may be oriented at an acute angle to the longitudinal axis (not shown). In such a case, the disk 762 may be oval or elliptical rather than circular.

The disk 762 includes any suitable material configured to prevent blood, emboli and other fluids from passing, and this thereby assists in occluding the body vessel 760. In one embodiment, the disk 762 may be made of nylon, rayon, polyester, biocompatible polyurethanes, polytetrafluoroethylene (known as PTFE or under the trade name Teflon™), and mixtures thereof without falling beyond the scope or spirit of the present invention. In one example, the material may be made of one material and coated with another, such as the biocompatible polyurethane. In another example, the occluding barrier may be made of connective tissue material including, for example, extracellular matrix (ECM), which is described above.

One example of the biocompatible polyurethane is sold under the trade name THORALON (THORATEC, Pleasanton, Calif.). Descriptions of suitable biocompatible polyureaurethanes are described in U.S. Pat. Application Publication No. 2002/0065552 A1 and U.S. Pat. No. 4,675,361, both of which are herein incorporated by reference. Briefly, these publications describe a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be manipulated to provide either porous or non-porous THORALON. The present invention envisions the use of non-porous THORALON. Non-porous THORALON can be formed by mixing the polyetherurethane urea (BPS-215) and the surface modifying additive (SMA-300) in a solvent, such as dimethyl formamide (DMF), tetrahydrofuran (THF), dimethyacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold. In one example, the composition can be dried to remove the solvent.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes/polycarbamates and urea linkages (hereinafter "—C(O)N or CON type polymers") may also be employed. These include CON type polymers that preferably include a soft segment and a hard segment. The segments can be combined as copolymers or as blends. For example, CON type polymers with soft segments such as PTMO, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

Preferably, the hard segment is formed from a diisocyanate and diamine. The diisocyanate may be represented by the formula OCN—R—NCO, where —R— may be aliphatic, aromatic, cycloaliphatic or a mixture of aliphatic and aromatic moieties. Examples of diisocyanates include MDI, tetramethylene diisocyanate, hexamethylene diisocyanate, trimethylhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3'-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, 1,6-hexanediol, 1,8-octanediol, propylene glycols, 2,3-butylene glycol, dipropylene glycol, dibutylene glycol, glycerol, or mixtures thereof.

Biocompatible CON type polymers modified with cationic, anionic and aliphatic side chains may also be used. See, for example, U.S. Pat. No. 5,017,664. Other biocompatible CON type polymers include: segmented polyurethanes, such as BIOSPAN; polycarbonate urethanes, such as BIONATE; and polyetherurethanes, such as ELASTHANE; (all available from POLYMER TECHNOLOGY GROUP, Berkeley, Calif.).

Other biocompatible CON type polymers can include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; and aliphatic, hydroxy-terminated polycarbonate.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference. As noted above, the occluding barrier may also be made of connective tissue material including, for example, an ECM such as SIS.

In another embodiment (not shown), there could be two disks 762, wherein each one is attached to an end 744, 748 of the tubular expandable body 732. In such an embodiment, there could be a single restricting ring 734 located around the middle portion 746 of the tubular expandable body 732.

Figure 12:
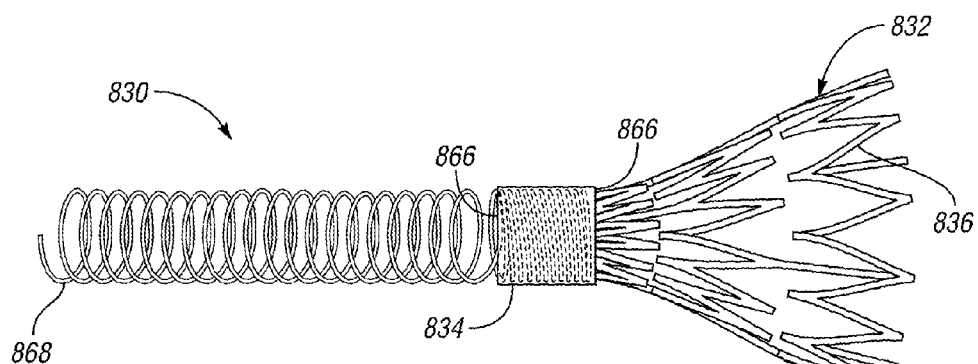
FIG. 12 is a side view of still another occlusion device according to the principles of the present invention.

Now with reference to FIG. 12, yet another occlusion device 830 embodying the principles of the present invention is illustrated. Like the occlusion devices 30, 130, 230, 330, 430, 530, 630, 730 previously described, the occlusion device 830 of FIG. 12 has a tubular expandable body 832 comprising a plurality of members 836 that is configured to move between an expanded state and a collapsed state, and a restricting ring 834 (such as the marker band shown) collapsing a portion of the tubular expandable body 832. In this embodiment, the restricting ring 834 is located at an end of the tubular expandable body 832 such that the tubular expandable body 832 extends from a side 866 of the restricting ring 834. A coil 868 extends from an opposite side 866 of the restricting ring 834. The coil 868 is preferably helical in shape, and may be formed of any suitable material, such as, for example, a superelastic material, a nickel-based superalloy, stainless steel wire, cobalt-chromium-nickel-molybdenum-iron alloy, cobalt chrome-alloy, stress relieved metal (e.g., platinum), or nickel-based superalloys, such as Inconel. In addition, the coil 868 may have occluding material (not shown), such as Dacron or SIS, attached thereto. The occluding material may be attached to the coil 868 in any suitable manner, for example, the occluding material may be mechanically fixated to the coil 868.

Figure 13:
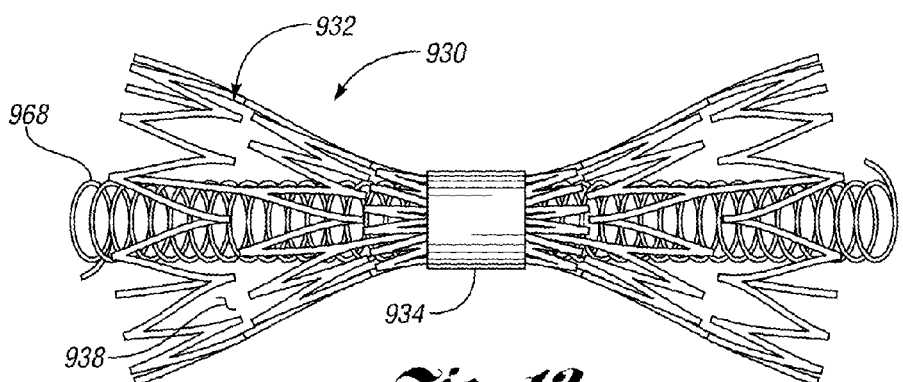
FIG. 13 is a side view of still another occlusion device according to the principles of the present invention.

With reference to FIG. 13, another occlusion device 930 is illustrated. Similarly to the occlusion device 830 of FIG. 12, the occlusion device 930 includes a tubular expandable body 932, a marker band 934, and a coil 968. In this embodiment, the coil 968 extends through the center of the lumen 938 of the tubular expandable body 932 along the longitudinal axis of the occlusion device 930. The marker band 934 (or any other restricting ring that is used) collapses a portion of the tubular expandable body 932 around the coil 968 to substantially close the lumen 938 of the tubular expandable body 932 and fasten the coil 968 to the tubular expandable body 932. Occluding material, such as the types hereinbefore described, could also be added to further aid in occluding a body vessel.

Figure 14:
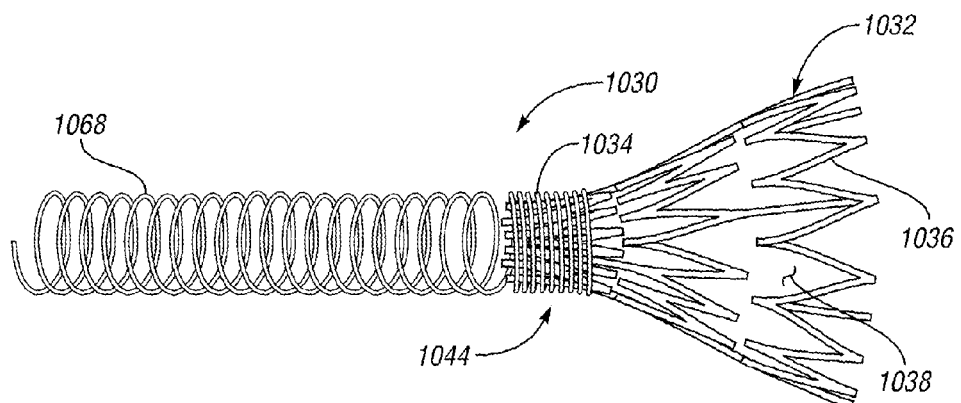
FIG. 14 is a side view of still another occlusion device according to the principles of the present invention.

With reference to FIG. 14, yet another occlusion device 1030 is illustrated. The occlusion device 1030 has a tubular expandable body 1032 similar to the tubular expandable bodies 32, 132, 232, 332, 432, 532, 632, 732, 832, 932 hereinbefore described. As such, the tubular expandable body 1032 has a plurality of members 1036 that are configured to move between an expanded state and a collapsed state. A coil extends from an end 1044 of the tubular expandable body 1032. The coil 1068 may be substantially similar to the coil 968 of FIG. 13. However, in this embodiment, the coil 1068 serves as a restricting ring to collapse a portion of the tubular expandable body 1032. The restricting ring portion 1034 of the coil 1068 is wrapped around the end 1044 of the tubular expandable body 1032 to substantially close the lumen 1038 of the tubular expandable body 1032. The restricting ring portion 1034 may be attached to the tubular expandable body 1032 in any suitable manner, such as those manners hereinbefore described with reference to the restricting ring 34 of FIGS. 2a-4.

Figure 15:
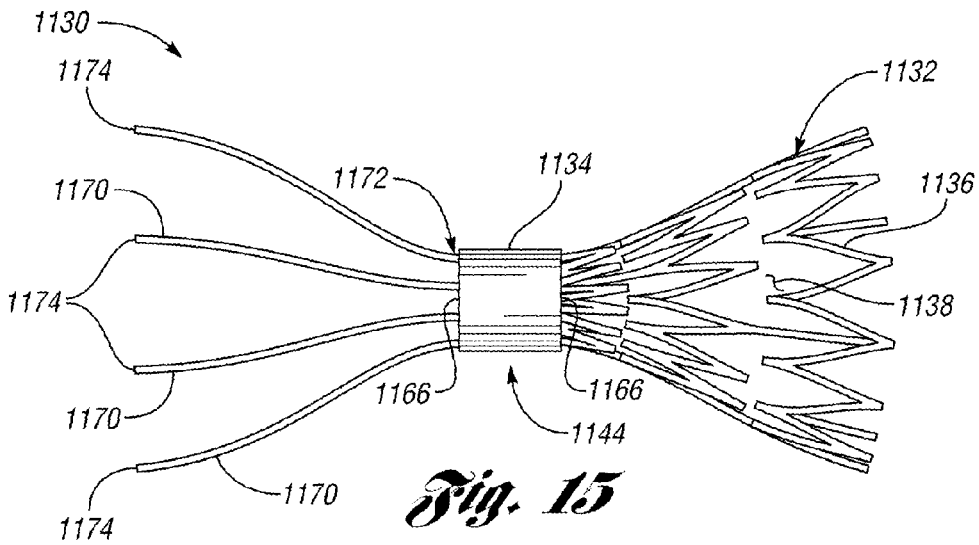
FIG. 15 is a side view of still another occlusion device according to the principles of the present invention.

Now with reference to FIG. 15, another occlusion device 1130 is illustrated. Like the occlusion devices 30, 130, 230, 330, 430, 530, 630, 730, 830, 930, 1030, the occlusion device 1130 of FIG. 15 has tubular expandable body 1132 having a plurality of members 1136 that are configured to move between an expanded state and a collapsed state. Further, the occlusion device 1130 has a restricting ring 1134, such as a marker band or any other type of restricting ring such as those hereinbefore described, collapsing an end 1144 of the tubular expandable body 1132 to substantially close the lumen 1138 of the tubular expandable body 1132. As such, the tubular expandable body 1132 extends from a side 1166 of the restricting ring 1134. From an opposite side 1166 of the restricting ring 1134, a plurality of spaced apart arcuate legs 1170 extends. The plurality of arcuate legs 1170 has attached together ends 1172, the attached together ends 1172 being attached together by the restricting ring 1134 or in any other suitable manner. In the alternative, the ends 1172 contacting the restricting ring 1134 could merely be attached to the restricting ring 1134 or the tubular expandable body 1132 without being attached together.

The plurality of arcuate legs 1170 also free ends 1174, which extend outward toward the vessel wall in the expanded state. In other words, a middle portion of each arcuate leg 1170 extends radially away from the longitudinal axis when the occlusion device 1130 is in the expanded state, for example, when deployed within the body vessel 760 as shown in FIG. 11. Thus, the arcuate legs 1170 are configured to move between an expanded state and a collapsed state, for device 1130 use and device 1130 retrieval and delivery, respectively. While the exact number of the arcuate legs 1170 may vary depending on the needs of a particular application, the present example illustrates four arcuate legs 1170.

Optionally, the arcuate legs 1170 may also include anchoring members (not shown). The anchoring members may have any appropriate shape to keep the device 1130 from moving within the body vessel. The anchoring members could be configured as barbs or hooks, for example.

Figure 16:
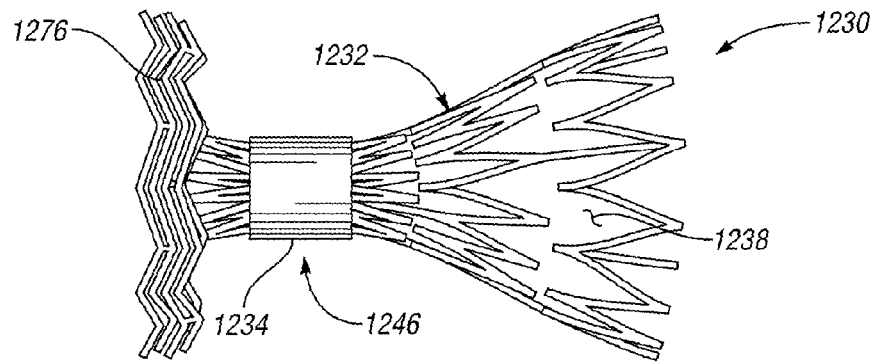
FIG. 16 is a side view of still another occlusion device according to the principles of the present invention.

Now with reference to FIG. 16, another occlusion device 1230 is illustrated. The occlusion device 1230 includes a tubular expandable body 1232 having a middle portion 1246 collapsed by a restricting ring 1234. On one side of the restricting ring 1234, the tubular expandable body 1232 is heat treated and then quenched, which allows the heat treated portion to be set as a longitudinally compressed portion 1276 of the tubular expandable body 1232. Heat treating the tubular expandable body 1232 may help hold the shape of the tubular expandable body 1232 and remove some of the spring force therein, depending on the material that the tubular expandable body 1232 is comprised of. The longitudinally compressed portion 1276 may be superior in its occluding abilities, as it may consume more of the vessel cross section and close the lumen 1238 of the tubular expandable body 1232. The shape of the occlusion device 1230 may be described as a wine glass shape. In all other respects, the occlusion device 1230 may be similar to any of the other occlusion devices hereinbefore or hereinafter described, including any of the variations thereof. For example, the occlusion device 1230 could comprise occluding material, such as that shown in FIGS. 5-11.

In another embodiment, the tubular expandable body 1232 could be formed into the shape shown in FIG. 16 by cold working, instead of heat treating. The cold working could help hold the shape of the tubular expandable body 1232 and remove some of the spring force therein.

Figure 17:
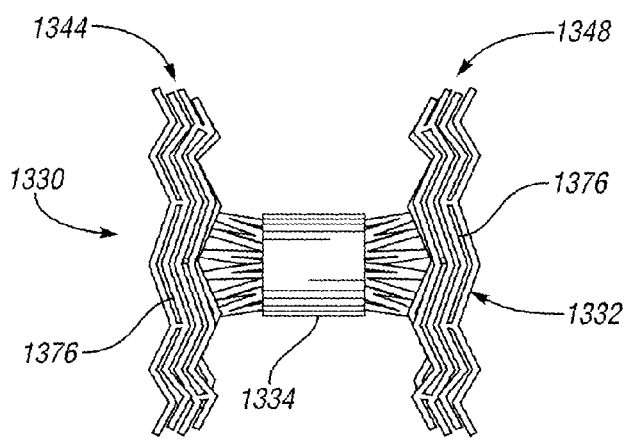
FIG. 17 is a side view of still another occlusion device according to the principles of the present invention.

With reference to FIG. 17, another occlusion device 1330 is illustrated, which is substantially similar to the occlusion device 1230 of FIG. 16. As such, the occlusion device 1330 of FIG. 17 has a tubular expandable body 1332 that is partially collapsed by a restricting ring 1334. Both the proximal portion 1344 and the distal portion 1348 are heat treated to form longitudinally compressed portions 1376, which are similar to the longitudinally compressed portion 1276 of FIG. 16. In the alternative, the longitudinally compressed portions 1376 could be formed by cold working, instead of heat treating. The shape of the occlusion device 1330 may be described as a spool shape, which has two flat ends and a cylindrical center. In all other respects, the occlusion device 1330 may be similar to those hereinbefore or hereinafter described.

Figure 18:
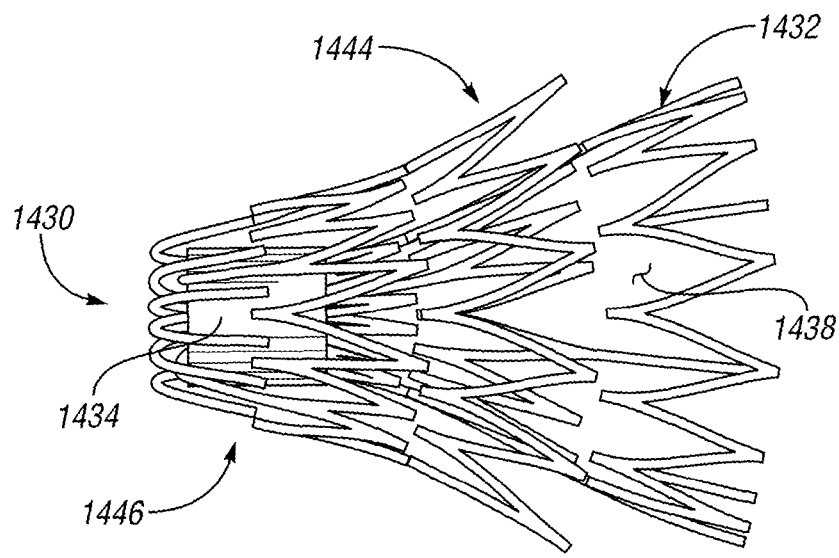
FIG. 18 is a side view of still another occlusion device according to the principles of the present invention.

Now with reference to FIG. 18, yet another occlusion device 1430 is illustrated. The occlusion device 1430 includes a tubular expandable body 1432, which is collapsed in a middle portion 1446 by a restricting ring 1434. In this embodiment, it is preferably that the restricting ring 1434 substantially closes the lumen 1438 of the tubular expandable body 1432. In this embodiment, one end 1444 of the tubular expandable body 1432 is folded over the restricting ring 1434 and heat treated. After heat treating, the tubular expandable body 1432 stays folded over the restricting ring 1434. In the alternative, the tubular expandable body 1432 could be cold worked, instead of heat treated. The shape of the occlusion device 1430 may be described as a flower shape.

Figure 19:
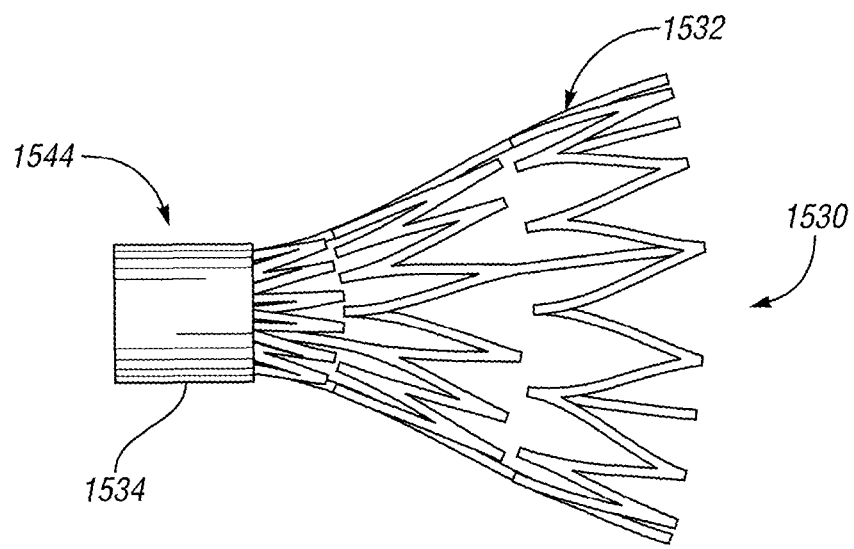
FIG. 19 is a side view of still another occlusion device according to the principles of the present invention.

Now with reference to FIG. 19, yet another occlusion device 1530 is illustrated. The occlusion device 1530 has a tubular expandable body 1532, which is collapsed at one end 1544 by a restricting ring 1534. Thus, the occlusion device 1530 has a Christmas tree, or fir tree, shape. In all other respects, the occlusion device 1530 may be similar to those hereinbefore or hereinafter described.

Figure 20:
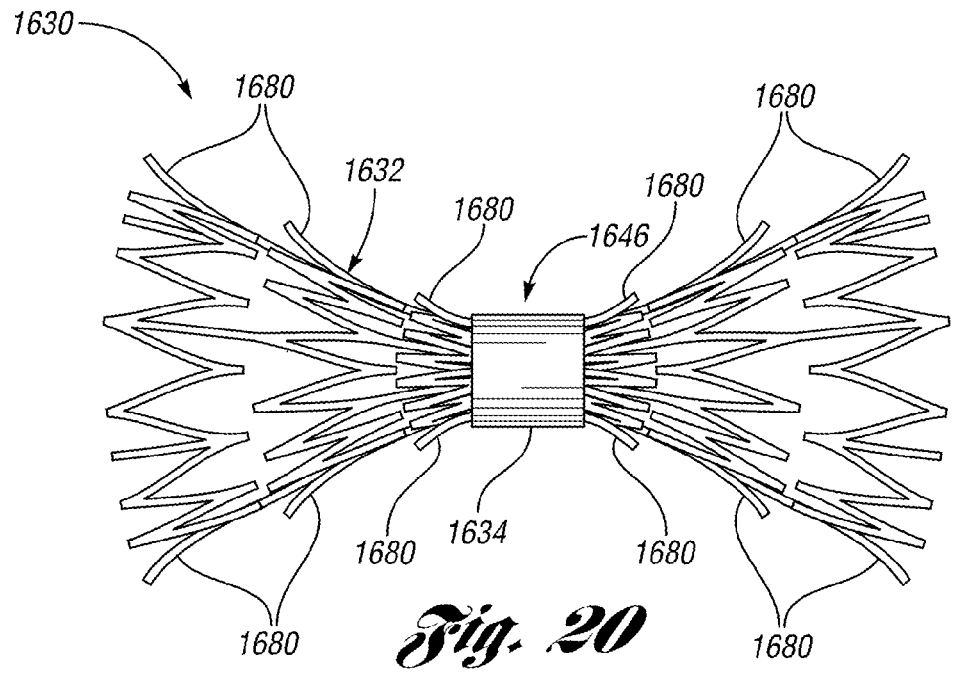
FIG. 20 is a side view of still another occlusion device according to the principles of the present invention.

With reference to FIG. 20, still another occlusion device 1630 is illustrated. Like the occlusion devices hereinbefore described, the occlusion device 1630 has a tubular expandable body 1632 that is collapsed in a middle portion 1646 by a restricting ring 1634. In this embodiment, the tubular expandable body 1632 has exterior portions 1680 bent outward to contact the vessel wall in the expanded state. The exterior portions 1680 could be bent outward, heated outward, or otherwise formed to contact the vessel wall in a manner more secure than merely contacting the vessel wall due to radial force. In the alternative, it should be understood that any of the occlusion devices described herein could be configured to contact the vessel wall to secure the occlusion device to the vessel wall by simply configuring the tubular expandable body to provide a radial force to press the occlusion device into the vessel wall. In all other respects, the occlusion device 1630 may be similar to those hereinbefore or hereinafter described.

Figure 21:
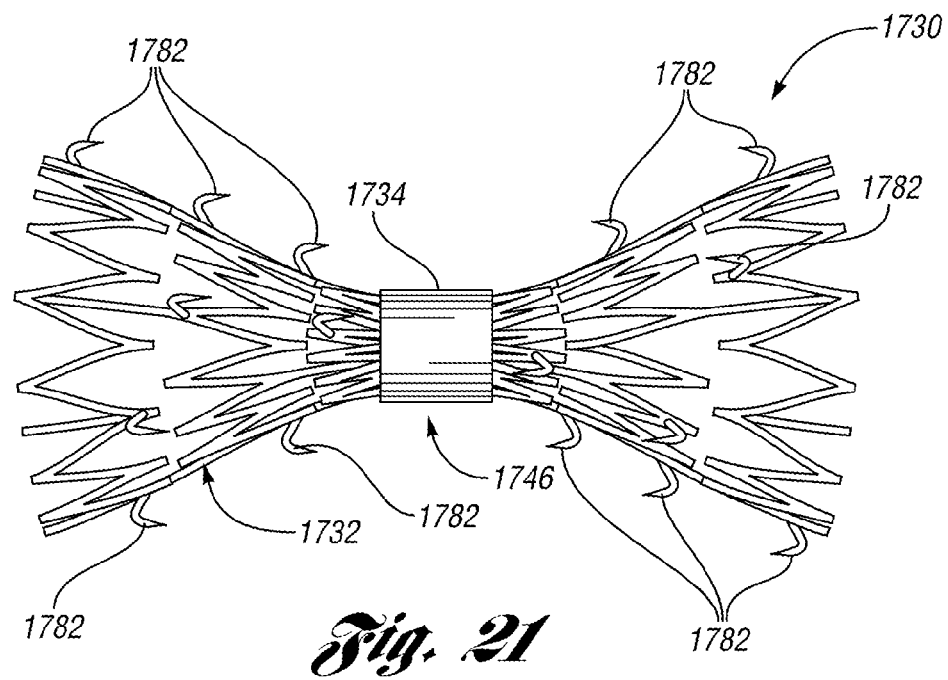
FIG. 21 is a side view of still another occlusion device according to the principles of the present invention.

With reference to FIG. 21, another occlusion device 1730 is illustrated. Like the occlusion devices hereinbefore described, the occlusion device 1730 has a tubular expandable body 1732 collapsed in a middle portion 1746 by a restricting ring 1734. The tubular expandable body 1732 has barbs or hooks 1782 on an exterior side of the tubular expandable body 1732 to aid in anchoring the occlusion device 1730 to the vessel wall. It should be understood that any other suitable anchoring members could alternatively or additionally be used. In all other respects, the occlusion device 1730 may be similar to those hereinbefore or hereinafter described.

In any occlusion device described herein, the tubular expandable body could comprise a plurality of portions having varying amounts of stiffness. In order to have varying amounts of stiffness, a tubular expandable body could have members which have different thicknesses or a thickness that varies along the length of a member. In addition, or in the alternative, part of the tubular expandable body, as used for the invention herein, could be annealed to make parts of the body structure softer. In another variation, the tubular expandable body could have a varying wire design, or different kinds of cuts, to provide areas that are softer than others.

Figures 22A, 22B:
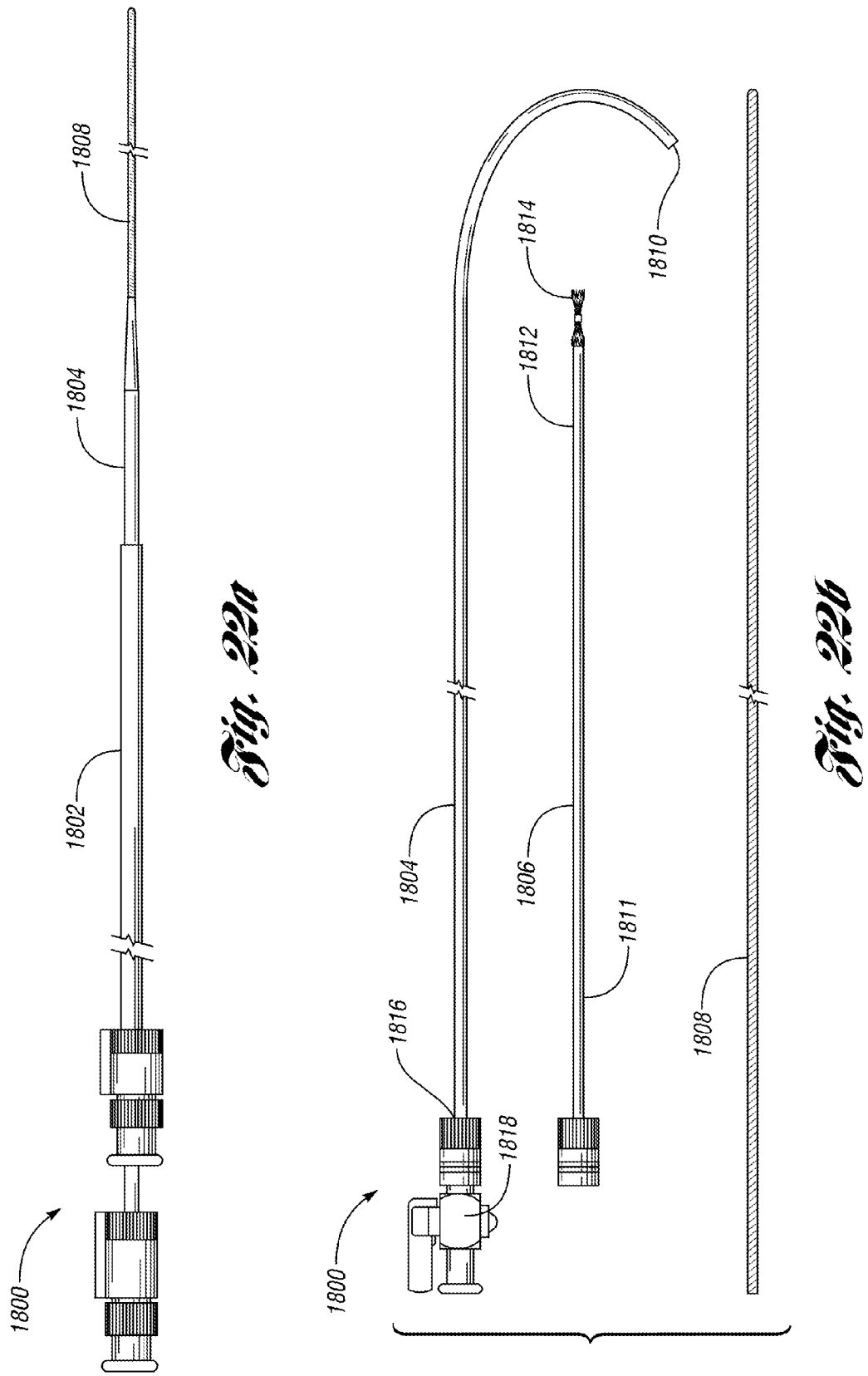
FIG. 22a is a side view of a delivery and retrieval assembly for use with the occlusion device, in accordance with the principles of the present invention.
FIG. 22b is an exploded view of the delivery and retrieval assembly of FIG. 22a, in accordance with the principles of the present invention.

FIGS. 22a and 22b depict a delivery assembly 1800 for introducing and retrieving the occlusion device for occluding a body vessel in accordance with another embodiment of the present invention. As shown, the delivery assembly 1800 includes a polytetrafluoroethylene (PTFE) introducer sheath 1802 for percutaneously introducing an outer sheath 1804 (equivalent to the sheath 50 described above) into a body vessel. Of course, any other suitable material for the introducer sheath 1802 may be used without falling beyond the scope or spirit of the present invention. The introducer sheath 1802 may have any suitable size, for example, between about three-french to eight-french. The introducer sheath 1802 serves to allow the outer sheath 1804 and an inner member or catheter 1806 to be percutaneously inserted to a desired location in the body vessel. The inner member may also include, for example, a stylet. The introducer sheath 1802 receives the outer sheath 1804 and provides stability to the outer sheath 1804 at a desired location of the body vessel. For example, the introducer sheath 1802 is held stationary within a common visceral artery, and adds stability to the outer sheath 1804, as the outer sheath 1804 is advanced through the introducer sheath 1802 to an occlusion area in the vasculature. The outer sheath 1804 has a body extending from a proximal end 1816 to a distal end 1810, the body being tubular and including a sheath lumen extending therethrough.

As shown, the assembly 1800 may also include a wire guide 1808 configured to be percutaneously inserted within the vasculature to guide the outer sheath 1804 to the occlusion area. The wire guide 1808 provides the outer sheath 1804 with a path to follow as it is advanced within the body vessel. The size of the wire guide 1808 is based on the inside diameter of the outer sheath 1804 and the diameter of the target body vessel.

When the distal end 1810 of the outer sheath 1804 is at the desired location in the body vessel, the wire guide 1808 is removed and the occlusion device 1814, having a proximal segment contacting a distal portion 1812 of the inner catheter 1806, is inserted into the outer sheath 1804. The inner catheter 1806 is advanced through the outer sheath 1804 for deployment of the occlusion device 1814 through the distal end 1810 to occlude the body vessel during treatment of, for example, an aneurism, or to otherwise occlude a body vessel. The catheter 1806 extends from a proximal portion 1811 to a distal portion 1812 and is configured for axial movement relative to the outer sheath 1804. In this example, the distal portion 1812 is shown adjacent to an occlusion device 1814 (similar to any of the occlusion devices described above). Thus, before deployment, the occlusion device 1814 is coaxially disposed within the lumen of the outer sheath 1804 and removably coupled to the distal portion 1812 of the catheter 1806, or in the alternative, the occlusion device 1814 is merely pushed by, but not coupled to, the distal portion 1812 of the catheter 1806.

The outer sheath 1804 further has a proximal end 1816 and a hub 1818 to receive the inner catheter 1806 and occlusion device 1814 to be advanced therethrough. The size of the outer sheath 1804 is based on the size of the body vessel in which it percutaneously inserts, and the size of the occlusion device 1814.

In this embodiment, the occlusion device 1814 and inner catheter 1806 are coaxially advanced through the outer sheath 1804, following removal of the wire guide 1808, in order to position the occlusion device 1814 to occlude the body vessel. The occlusion device 1814 is guided through the outer sheath 1804 by the inner catheter 1806, preferably from the hub 1818, and exits from the distal end 1810 of the outer sheath 1804 at a location within the vasculature where occlusion is desired. Thus, the occlusion device 1814 is deployable through the distal end 1810 of the outer sheath 1804 by means of axial relative movement of the catheter 1806. In order to more easily deploy the occlusion device 1814 into the body vessel, the occlusion device 1814 may have a slippery coating, such as Silicone or slipcoating.

Likewise, this embodiment may also retrieve the occlusion device 1814 by positioning the distal end 1810 of the outer sheath 1804 adjacent the deployed device 1814 in the vasculature. The inner catheter 1806 is advanced through the outer sheath 1804 until the distal portion 1812 protrudes from the distal end 1810 of the outer sheath 1804. The distal portion 1812 is coupled to a proximal end of the occlusion device 1814, after which the inner catheter 1806 is retracted proximally, drawing the occlusion device 1814 into the outer sheath 1804.

It is understood that the assembly described above is merely one example of an assembly that may be used to deploy the occlusion device in a body vessel. Of course, other apparatus, assemblies and systems may be used to deploy any embodiment of the occlusion device without falling beyond the scope or spirit of the present invention.

Figure 23:
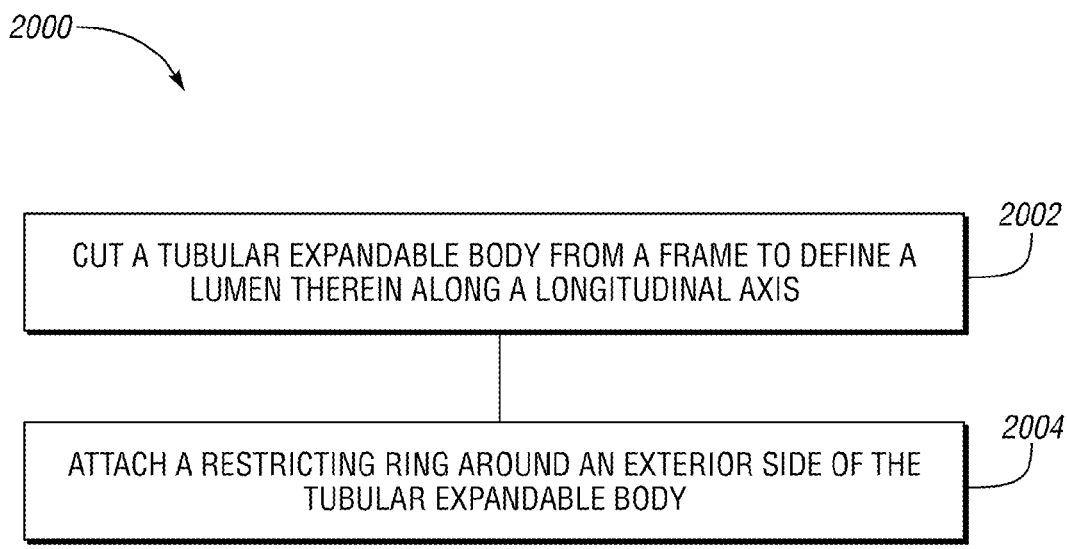
FIG. 23 is a block diagram describing a method of constructing an occlusion device, in accordance with the principles of the present invention.

Turning to FIG. 23, the present invention further provides a method 2000 of constructing an occlusion device for occluding a body vessel. The method 2000 includes a step 2002 of cutting a tubular expandable body from a frame to form the tubular expandable body defining a lumen along a longitudinal axis through a center of the tubular expandable body and a step 2004 of attaching a restricting ring around an exterior side of the tubular expandable body. The method 2000 could further include adding occluding material, of the various types described above. In addition, the method 2000 could further include heat treating the tubular expandable body. In the alternative, the method 2000 could further include cold working the tubular expandable body.

As a person skilled in the art will readily appreciate, the above description is meant as an illustration of implementation of the principles this invention. This description is not intended to limit the scope or application of this invention in that the invention is susceptible to modification, variation and change, without departing from the spirit of this invention, as defined in the following claims.

I claim:

1. An occlusion device for occluding a body vessel, the occlusion device comprising:
   a tubular expandable body having an interior side and an exterior side, the tubular expandable body defining a lumen formed through a center of the tubular expandable body along the longitudinal axis of the occlusion device, the lumen extending from a first completely open end to a second completely open end;
   a restricting ring disposed around the exterior side of the tubular expandable body and collapsing a portion of the tubular expandable body; and
   occluding material attached to at least one of the tubular expandable body and the restricting ring to completely occlude the body vessel, the occluding material including at least one of nylon, rayon, polytetrafluoroethylene, and extracellular matrix,
   the tubular expandable body being configured to move between an expanded state for occlusion within a body vessel and a collapsed state for delivery or retrieval of the device, the tubular expandable body being configured to open radially to define the expanded state and to collapse along a longitudinal axis to define the collapsed state,
   the occlusion device having a collapsed portion and an uncollapsed portion, the collapsed portion having the restricting ring disposed around the exterior side of the tubular expandable body and the uncollapsed portion having the tubular expandable body without the restricting ring disposed around its exterior side, the collapsed portion having a diameter that is smaller than the diameter of the uncollapsed portion when the tubular expandable body is in the expanded state.

2. The occlusion device of claim 1, wherein the occluding material is woven under and over members of the tubular expandable body.

3. The occlusion device of claim 1, wherein the occluding material extending through the center of the tubular expandable body at least partially along the longitudinal axis, the restricting ring collapsing the portion of the tubular expandable body to substantially close the lumen of the tubular expandable body around the occluding material, the occluding material being held by the restricting ring.

4. The occlusion device of claim 1, wherein the occluding material includes extracellular matrix.

5. The occlusion device of claim 4, the occluding material including submucosa.

6. The occlusion device of claim 1, wherein the restricting ring is one of an SIS strand, a flexible tube, and an elastic band.

7. The occlusion device of claim 1, wherein the tubular expandable body comprises a plurality of portions, the portions having varying amounts of stiffness.

8. The occlusion device of claim 1, the tubular expandable body being an outer tubular expandable body defining a lumen through a center of the outer tubular expandable body along the longitudinal axis of the occlusion device, the occlusion device further comprising an inner tubular expandable body extending through the center of the outer tubular expandable body, the restricting ring further collapsing a portion of the inner tubular expandable body, the inner and outer tubular expandable bodies being self-expanding.

9. The occlusion device of claim 8, wherein the occluding material is attached to the occlusion device between the outer tubular expandable body and the inner tubular expandable body.

10. The occlusion device of claim 1, wherein at least a portion of the tubular expandable body is heat treated.

11. The occlusion device of claim 1, the tubular expandable body having a middle portion disposed about halfway between the first and second open ends, the middle portion having a middle diameter, the first open end having a first diameter, and the second open end having a second diameter, the restricting ring collapsing at least part of the middle portion of the tubular expandable body, such that the middle diameter is smaller than the first and second diameters in the expanded state.

12. An occlusion device for occluding a body vessel, the occlusion device comprising:
   a tubular expandable body having an interior side and an exterior side, the tubular expandable body defining a lumen formed through a center of the tubular expandable body along the longitudinal axis of the occlusion device, the lumen extending from a first completely open end to a second completely open end;
   a restricting ring disposed around the exterior side of the tubular expandable body and collapsing a portion of the tubular expandable body; and
   occluding material attached to at least one of the tubular expandable body and the restricting ring to completely occlude the body vessel, the occluding material including at least one of nylon, rayon, polytetrafluoroethylene, and extracellular matrix, the occluding material is configured as a disk attached to the interior side of the tubular expandable body,
   the tubular expandable body being configured to move between an expanded state for occlusion within a body vessel and a collapsed state for delivery or retrieval of the device, the tubular expandable body being configured to open radially to define the expanded state and to collapse along a longitudinal axis to define the collapsed state.

13. An occlusion device for occluding a body vessel, the occlusion device comprising:
a tubular expandable body having an interior side and an exterior side;
a restricting ring being disposed around the exterior side of the tubular expandable body and collapsing a portion of the tubular expandable body; and
a coil attached directly to and extending from the tubular expandable body,
the tubular expandable body being configured to move between an expanded state for occlusion within a body vessel and a collapsed state for delivery or retrieval of the device, the tubular expandable body being configured to open radially to define the expanded state and to collapse along a longitudinal axis to define the collapsed state,
the occlusion device having a collapsed portion and an uncollapsed portion, the collapsed portion having the restricting ring disposed around the exterior side of the tubular expandable body and the uncollapsed portion having the tubular expandable body without the restricting ring disposed around its exterior side, the collapsed portion having a diameter that is smaller than the diameter of the uncollapsed portion when the tubular expandable body is in the expanded state.

14. The occlusion device of claim 13, wherein the tubular expandable body defines a lumen through a center of the tubular expandable body along the longitudinal axis of the occlusion device, the coil extending through the center of the tubular expandable body at least partially along the longitudinal axis, the restricting ring collapsing the portion of the tubular expandable body to substantially close the lumen of the tubular expandable body around the coil and cause the coil to be attached to the tubular expandable body at the restricting ring.

15. An occlusion device for occluding a body vessel, the occlusion device comprising:
a tubular expandable body having an interior side and an exterior side, the tubular expandable body extending from a first end to a second end, the tubular expandable body comprising a frame having a plurality of members that are interconnected with each other at both the first and second ends;
a restricting ring disposed around the exterior side of the tubular expandable body and collapsing a portion of the tubular expandable body at the first end of the tubular expandable body, the tubular expandable body being open at the second end of the tubular expandable body; and
a plurality of spaced apart arcuate legs attached to and freely extending from at least one of the restricting ring and the tubular expandable body, the plurality of arcuate legs having free ends,
the tubular expandable body being configured to move between an expanded state for occlusion within a body vessel and a collapsed state for delivery or retrieval of the device and to completely occlude the body vessel, the tubular expandable body being configured to open radially to define the expanded state and to collapse along a longitudinal axis to define the collapsed state,
the occlusion device having a collapsed portion and an uncollapsed portion, the collapsed portion having the restricting ring disposed around the exterior side of the tubular expandable body and the uncollapsed portion having the tubular expandable body without the restricting ring disposed around its exterior side, the collapsed portion having a diameter that is smaller than the diameter of the uncollapsed portion when the tubular expandable body is in the expanded state.

16. The occlusion device of claim 15, wherein the arcuate legs include anchoring members configured to keep the occlusion device from moving within the body vessel.

17. An occlusion device for occluding a body vessel, the occlusion device comprising:
a tubular expandable body having an interior side and an exterior side, the tubular expandable body having a middle portion disposed between first and second completely open ends and located about halfway between the first and second open ends, the tubular expandable body having a lumen that extends from the first completely open end to the second completely open end, the middle portion having a middle diameter, the first open end having a first diameter, and the second open end having a second diameter, the tubular expandable body being configured to move between an expanded state for occlusion within a body vessel and a collapsed state for delivery or retrieval of the device and to completely occlude the body vessel, the tubular expandable body being configured to open radially to define the expanded state and to collapse along a longitudinal axis to define the collapsed state; and
a restricting ring disposed around the exterior side of the tubular expandable body and collapsing at least part of the middle portion of the tubular expandable body, such that the middle diameter is smaller than the first and second diameters in the expanded state,
the occlusion device having a collapsed portion and an uncollapsed portion, the collapsed portion having the restricting ring disposed around the exterior side of the tubular expandable body and the uncollapsed portion having the tubular expandable body without the restricting ring disposed around its exterior side, the collapsed portion having a diameter that is smaller than the diameter of the uncollapsed portion when the tubular expandable body is in the expanded state.

18. The occlusion device of claim 17, wherein the first and second diameters are about equal in the expanded state.

19. An occlusion device for occluding a body vessel, the occlusion device comprising:
a tubular expandable body defining a lumen through a center of the tubular expandable body;
a plurality of spaced apart arcuate legs attached to and extending from the tubular expandable body;
a single restricting ring disposed around the tubular expandable body and collapsing a portion of the tubular expandable body to substantially close the lumen of the tubular expandable body, the device being free of restricting rings other than the single restricting ring; and
occluding material attached to at least one of the tubular expandable body and the restricting ring to completely occlude the body vessel;
the tubular expandable being configured to move between an expanded state for occlusion within a body vessel and a collapsed state for delivery or retrieval of the device, the tubular expandable body being configured to open radially to define the expanded state and to collapse along a longitudinal axis to define the collapsed state,
the occlusion device having a collapsed portion and an uncollapsed portion, the collapsed portion having the restricting ring disposed around the exterior side of the tubular expandable body and the uncollapsed portion having the tubular expandable body without the restricting ring disposed around its exterior side, the collapsed portion having a diameter that is smaller than the diameter of the uncollapsed portion when the tubular expandable body is in the expanded state.

20. The occlusion device of claim 19, wherein the occluding material includes at least one of nylon, rayon, polytetrafluoroethylen, extracellular matrix, and mixtures thereof.

21. The occlusion device of claim 19, the tubular expandable body having a middle portion disposed between first and second open ends, the middle portion having a middle diameter, the first open end having a first diameter, and the second open end having a second diameter, the restricting ring collapsing at least part of the middle portion of the tubular expandable body, such that the middle diameter is smaller than the first and second diameters in the expanded state.

22. The occlusion device of claim 19, wherein a folded portion of the tubular expandable body is folded over the restricting ring, the folded portion contacting an outside surface of the restricting ring.

23. The occlusion device of claim 19, wherein a folded portion of the tubular expandable body is folded over the restricting ring, the folded portion being folded completely around the restricting ring.

24. A delivery assembly for placing and retrieving an occlusion device for occluding a body vessel, the assembly comprising:
an outer sheath having a body extending from a proximal part to a distal part, the body being tubular and forming a sheath lumen extending therethrough;
an inner member extending from a proximal portion to a distal portion, the inner member being disposed within the sheath lumen and configured for axial movement relative to the outer sheath;
the occlusion device being coaxially disposed within the sheath lumen and removably coupled to the distal portion of the inner member and deployable through the distal part of the outer sheath by means of the relative axial movement of the inner member, the occlusion device comprising:
a tubular expandable body having an interior side and an exterior side, the tubular expandable body having a middle portion disposed about halfway between first and second completely open ends, the tubular expandable body having a lumen that extends from the first completely open end to the second completely open end, the middle portion having a middle diameter, the first open end having a first diameter, and the second open end having a second diameter, the tubular expandable body being configured to move between an expanded state for occlusion within a body vessel and a collapsed state for delivery or retrieval of the device, the tubular expandable body being configured to open radially to define the expanded state and to collapse along a longitudinal axis to define the collapsed state; and
a restricting ring disposed around the exterior side of the tubular expandable body and collapsing at least part of the middle portion of the tubular expandable body, such that the middle diameter is smaller than the first and second diameters in the expanded state,
the occlusion device having a collapsed portion and an uncollapsed portion, the collapsed portion having the restricting ring disposed around the exterior side of the tubular expandable body and the uncollapsed portion having the tubular expandable body without the restricting ring disposed around its exterior side, the collapsed portion having a diameter that is smaller than the diameter of the uncollapsed portion when the tubular expandable body is in the expanded state.

25. The delivery assembly of claim 24, wherein the occlusion device further comprises occluding material attached to at least one of the tubular expandable body and the restricting ring.

* * * * *

UNITED STATES PATENT AND TRADEMARK OFFICE
CERTIFICATE OF CORRECTION

PATENT NO. : 8,764,772 B2
APPLICATION NO. : 12/034719
DATED : July 1, 2014
INVENTOR(S) : Tekulve Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1497 days.

Signed and Sealed this
Second Day of August, 2016

Michelle K. Lee
*Director of the United States Patent and Trademark Office*